United States Patent [19]

Schmitt et al.

[11] Patent Number: 5,329,040

[45] Date of Patent: Jul. 12, 1994

[54] PROCESS FOR THE CONTINUOUS PREPARATION OF AMINOARYL OR AMINOALKYL β-SULFATOETHYL SULFONES

[75] Inventors: Lothar Schmitt, Königstein/Taunus; Rüdiger Berthold, Bad Soden am Taunus, both of Fed. Rep. of Germany

[73] Assignee: Hoechst Aktiengesellschaft, Frankfurt, Fed. Rep. of Germany

[21] Appl. No.: 871,341

[22] Filed: Apr. 21, 1992

[30] Foreign Application Priority Data

Apr. 23, 1991 [DE] Fed. Rep. of Germany ....... 4113147

[51] Int. Cl.$^5$ ................. C07C 309/69; C07C 315/04; C07C 309/64
[52] U.S. Cl. ...................... 558/29; 558/31; 558/33; 558/41
[58] Field of Search .......... 558/29, 33, 31, 41

[56] References Cited

U.S. PATENT DOCUMENTS

| | | | |
|---|---|---|---|
| 3,024,258 | 3/1962 | Brooks et al. | 558/41 X |
| 4,346,046 | 8/1982 | Nishimura et al. | 260/458 |
| 4,482,501 | 11/1984 | Nishimura et al. | 260/458 |

FOREIGN PATENT DOCUMENTS 8905290 6/1989 World Int. Prop. O. ............ 558/33

OTHER PUBLICATIONS

Chem. Abs.; STN; EP-144701-A; Jun. 1985.
Chem. Abs.; STN; WO-8905290; Jun. 1989.

*Primary Examiner*—Marianne M. Cintins
*Assistant Examiner*—Michael B. Hydorn
*Attorney, Agent, or Firm*—Connolly and Hutz

[57] ABSTRACT

In the process for the continuous preparation of aminoaryl or aminoalkyl β-sulfatoethyl sulfones by reaction of the corresponding β-hydroxyethyl sulfones with sulfuric acid in a molar ratio of 1:1 to 1:1.15 at temperatures above 120° C. a mixture of a β-hydroxyethyl sulfone with sulfuric acid is supplied to a fluidized bed of end product produced by recycling and mechanical stirring. The mixture is reacted at 100° to 200° C.

14 Claims, 1 Drawing Sheet

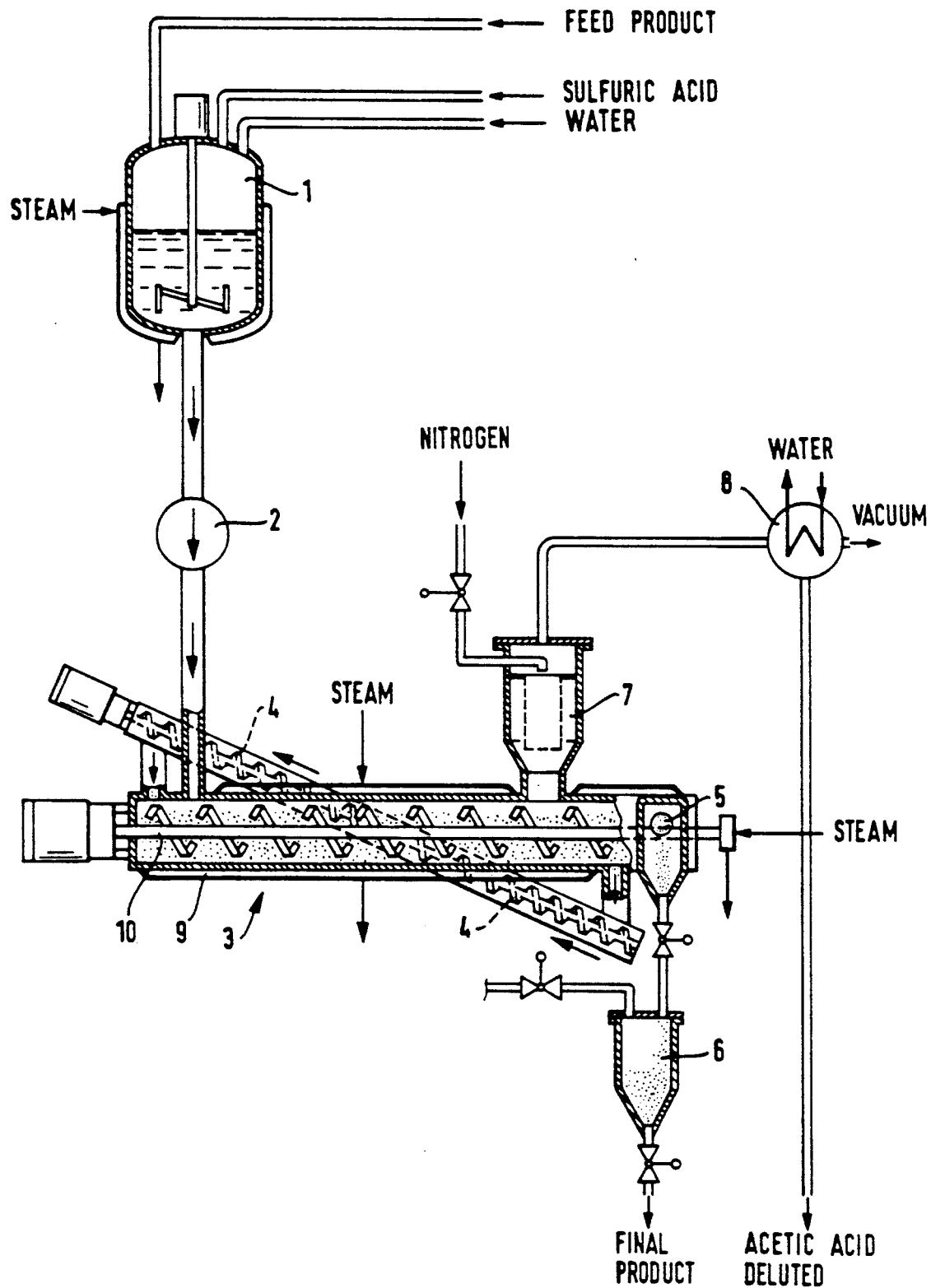

PROCESS FOR THE CONTINUOUS PREPARATION OF AMINOARYL OR AMINOALKYL β-SULFATOETHYL SULFONES

The invention relates to a process for the continuous preparation of aminoaryl or aminoalkyl β-sulfatoethyl sulfones by reaction of the corresponding β-hydroxyethyl sulfones with sulfuric acid in a molar ratio of 1:1 to 1:1.15 at temperatures above 120° C.

The preparation of aminoaryl or of aminoalkyl β-sulfatoethyl sulfones of the formula $$NH_2-A-SO_2-CH_2-CH_2-O-SO_3H$$

by esterification of the corresponding β-hydroxyethyl sulfones of the formula $$NH_2-A-SO_2-CH_2-CH_2-OH$$

in which A is an optionally substituted benzene or naphthalene radical or an alkyl group, with sulfuric acid is known. The esterification is customarily carried out in heated kneaders, on drying belts or in drying pans. As a result of the sensitivity of some products to heat, the temperature of the heating agent may be only slightly above the reaction temperature, which leads to residence times of several hours and a poor space-time yield. The products are obtained in the form of solidified sheets (drying belts) or granules containing lumps up to 40 mm in diameter (kneader, drying pan). The cement-like crust formation in the reaction apparatus gives rise to poor heat transfer conditions, which additionally prolongs the reaction time or further impairs the space-time yield. Moreover, high torques are required for the drives and these are often not sufficient to overcome the frictional forces between the mixing unit and the crusts.

The object is therefore to prevent the crust formation and to improve the space-time yields. This object is achieved by a process of the initially mentioned type in which a mixture of a β-hydroxyethyl sulfone with sulfuric acid is supplied to a fluidized bed of end product produced by recycling and mechanical stirring and is reacted at 100° to 200° C., preferably at 130°–180° C.

With this procedure 10 to 50% of the end product can be recycled into the fluidized bed. The reaction of the mixture can be carried out under pressures of between 50 and 100 mbar and with an average residence time of 15 to 300 minutes.

The advantages of the process are to be seen essentially in the better space-time yield, the shorter residence time and the resulting lower exposure to heat (higher product quality). In addition, the formation of plastic phases and crusts of end product is avoided. Reactor operation can be optimized in a simple manner by varying the amount of end product recycled.

BRIEF DESCRIPTION OF THE DRAWING

The sole FIGURE of the Drawing is a schematic representation of a preferred form of apparatus used to carry out the process of this invention.

DETAILED DESCRIPTION OF PREFERRED EMBODIMENT

The process is explained in more detail below with reference to the FIGURE.

In the stirred vessel 1, the starting components β-hydroxyethyl sulfones and sulfuric acid are mixed in a molar ratio of 1:1 to 1:1.15, with the optional addition of water, and are heated if necessary. The mixture is fed into the reactor 3 in a constant or pulsed stream by means of a volume-controllable pump 2. In said reactor 3 the mixture comes into contact with the granules fluidized by the stirrer 10, which granules are recycled from the reactor outlet to the reactor inlet by means of a screw conveyor 4. The reactor 3 may possess a system of rotary and stationary elements which clean one another and have a pronounced comminuting capacity. The reactor jacket 9 and the stirrer 10 are heatable and serve to heat the granules. The mixture of components pumped in impinges on the hot granules, which are fluidized by the stirrer 10 and recycled by the conveyor element 4, where, as a result of direct contact, they very rapidly reach the reaction temperature and solidify. Agglomerating end product is comminuted by the stirrer elements to give granules with a high proportion of fines.

The acetyl group which may be contained in the starting compound is split off during the reaction, with the formation of acetic acid, and escapes together with the water. The reaction can be considerably accelerated by lowering the pressure in the reaction space to 50 to 150 mbar, preferably 100 mbar.

The second half of the reactor 3 serves as a dwell chamber having a maximum temperature of up to 200° C. The reaction, which goes to completion here, is further activated by the grinding effect of the stirrer 10 and, if appropriate, the diffusion of the acetic acid and of the steam is improved by particle comminution and production of new fracture surfaces. The complete removal of the occluded volatile constituents thus takes place here. The residence time is determined by the outlet orifice 5, the height of which is adjustable, at the end of the reactor 3. The free-flowing end product flows through the orifice 5 into the intermediate container 6. The gaseous constituents and inert gases are passed through a filter 7 and separated from entrained dust. The dust can be blown back into the reaction space in phases using inert gas. The volatile constituents and water driven off can condense in the heat exchanger 8 and, optionally, can then be supplied for re-use.

EXAMPLE

A fluidized bed of end product was prepared in a reactor provided with a self-cleaning stirrer system and having a gross capacity of 15.4 l by initially introducing parabase ester (4-(β-sulfatoethylsulfonyl)aniline) in granule form and heated to 140° C. with stirring. Hot end product in granule form and the mixture, preheated to 80° C., of 4-(β-hydroxyethylsulfonyl)-1-acetylaminabenzene, sulfuric acid and water in a molar ratio of 1:1.05:2.5 were then fed simultaneously into the inlet zone of the reactor. The feed rate was 6.5 to 26 kg per hour, the average residence time of the product in the reactor was between 22 and 80 minutes, the pressure was 100 mbar, the temperature in the inlet zone was 125° to 135° C., in the center of the reactor was 155° to 165° C. and at the outlet was 170° to 180° C. and the reflux rate of product produced was 35%.

The product obtained was of the required quality. The following composition was determined using HPLC analysis:

| | |
|---|---|
| 4-(β-sulfatoethylsulfonyl)-1-aminobenzene | 97/98% |
| 4-(β-hydroxyethylsulfonyl)-1-acetylaminobenzene | <0.1% |
| 4-(β-hydroxyethylsulfonyl)-1-aminobenzene | 0.5/1.3% |
| 4-(β-acetoethylsulfonyl)-1-aminobenzene | 0.2/0.4% |

Different resident times which result because of the different feed rates have no influence on the quality data. The physical reaction conditions—temperature, pressure, speed of rotation—can be varied within a relatively wide range without a significant effect on the product characteristics.

We claim:

1. A process for the continuous preparation of aminoaryl or aminoalkyl β-sulfatoethyl sulfones of the formula $NH_2-A-SO_2CH_2CH_2-O-SO_3H$ in which A is an optionally substituted benzene or napthylene radical or an alkyl group, by reaction of the corresponding β-hydroxyethly sulfones with sulfuric acid in a molar ratio of 1:1 to 1:1.15 at temperatures above 120° C. wherein a mixture comprising β-hydroxyethyl sulfone and sulfuric acid is supplied to a mechanically generated fluidized bed of end product produced by recycling and mechanically stirring and is reacted at 100° to 200 ° C. and whereby the heat exchange is carried out indirectly.

2. The process as claimed in claim 1, wherein 10to 50% of the end product is recycled into the fluidized bed.

3. The process as claimed in claim 1, wherein the reaction of the mixture takes place under pressures of between 50 and 150 mbar.

4. The process as claimed in claim 1, wherein the reaction of the mixture takes place with average residence times of 15 to 300 minutes.

5. The process as claimed in claim 1, wherein the mixture further comprises water.

6. The process as claimed in claim 1, wherein the mixture is reacted at 130° to 180° C.

7. The process as claimed in claim 2, wherein the reaction of the mixture takes place under pressures of between 50 and 150 mbar.

8. The process as claimed in claim 3, wherein the reaction of the mixture takes place with average residence times of 15 and 300 minutes.

9. The process as claimed in claim 7, wherein the reaction of the mixture takes place with average residence times of 15 and 300 minutes.

10. A process for the continuous preparation of an amino-aryl or aminoalkyl β-sulfatoethyl sulfone from the corresponding β-hydroxyethylsulfone or an acylated derivative thereof, comprising the steps of:

providing a mechanically generated fluidized bed of the amino-aryl or aminoalkyl β-hydroxyethylsulfone end product in granulized form by recycling a portion of granules of the product produced by said process into a mechanically stirred zone wherein the fluidized bed containing said granules is maintained and wherein the temperature of the fluidized bed is in the range of about 100° to 200 ° C., providing a reaction mixture comprising the β-hydroxylsulfone corresponding to said end product or an acylated derivative thereof which, under the conditions in the mechanically stirred zone, splits off an acid which is volatile at the temperature of the fluidized bed, and sulfuric acid; wherein the β-hydroxylsulfone or acylated derivative thereof and the sulfuric acid is mixed in a molar ratio of about 1:1 to about 1:1.15; and introducing said reaction mixture into said fluidized bed, and carrying out the preparation of said end product substantially in said fluidized bed and whereby the heat exchange is carried out indirectly via a reactor housing 11. The process as claimed in claim 10, wherein the mechanical stirring which is used to provide the fluidized bed also comminutes agglomerates of said end product to give granules with a high proportion of fines.

12. The process as claimed in claim 10, wherein a portion of said end product is recovered from said mechanically stirred zone without being recycled into said fluidized bed.

13. The process as claimed in claim 10, wherein the starting material for producing said end product further comprises and acylated derivative of the corresponding β-hydroxyethyl sulfone; and the acid residue from said acylated derivative is volatilized in and permitted to escape from said fluidized bed.

14. The process as claimed in claim 13, wherein said reaction mixture contains water, and the water is also permitted to escape from said fluidized bed.

* * * * *